United States Patent
Jung et al.

(10) Patent No.: US 11,933,755 B2
(45) Date of Patent: Mar. 19, 2024

(54) ELECTROCHEMICAL APTASENSOR FOR DEHP DETECTION CONTAINING GOLD NANOFLOWERS

(71) Applicant: Industry-Academic Cooperation Foundation, Yonsei University, Seoul (KR)

(72) Inventors: Hyo-Il Jung, Seoul (KR); Kyungyeon Lee, Seoul (KR)

(73) Assignee: INDUSTRY-ACADEMIC COOPERATION FOUNDATION, YONSEI UNIVERSITY, Seoul (KR)

(*) Notice: Subject to any disclaimer, the term of this patent is extended or adjusted under 35 U.S.C. 154(b) by 0 days.

(21) Appl. No.: 18/054,340

(22) Filed: Nov. 10, 2022

(65) Prior Publication Data

US 2023/0142624 A1    May 11, 2023

(30) Foreign Application Priority Data

Nov. 11, 2021    (KR) .................. 10-2021-0154747

(51) Int. Cl.
*G01N 27/327*    (2006.01)
*C25D 3/48*    (2006.01)
(Continued)

(52) U.S. Cl.
CPC .......... *G01N 27/3276* (2013.01); *C25D 3/48* (2013.01); *C25D 5/48* (2013.01); *C25D 7/00* (2013.01); *G01N 27/308* (2013.01); *G01N 27/3278* (2013.01); *G01N 33/5308* (2013.01); *G01N 33/5438* (2013.01)

(58) Field of Classification Search
CPC ............. G01N 27/3276; G01N 27/308; G01N 27/3278; G01N 33/5308; G01N 33/5438; G01N 27/3277; G01N 33/442; C25D 3/48; C25D 5/48; C25D 7/00; B82Y 15/00; B82Y 30/00

See application file for complete search history.

(56) References Cited

U.S. PATENT DOCUMENTS 10,309,961 B2    6/2019    Ahn et al.
2017/0285017 A1    10/2017    Ahn et al.

FOREIGN PATENT DOCUMENTS

KR    20130066138 A    6/2013
KR    20170112305 A    10/2017
KR    20210105025 A    8/2021

OTHER PUBLICATIONS

M.-H. Lee, et al., "2D Materials in Development of Electrochemical Point-of-Care Cancer Screening Devices", Micromachines, 10(10): p. 662-1-662-40, Sep. 2019.*

(Continued)

*Primary Examiner* — J. Christopher Ball
(74) *Attorney, Agent, or Firm* — DICKINSON WRIGHT PLLC

(57) ABSTRACT

Provided is an electrochemical aptasensor for detecting di(2-ethylhexyl)phthalate (DEHP) with high sensitivity. The electrochemical aptasensor according to the present invention has a low detection limit concentration by improving sensitivity by sensor surface modification using a nano composite and gold nanoflowers, and has high practical applicability of a sensor by monitoring a trace amount of DEHP migrating from a real plastic product by a simple measurement method.

8 Claims, 8 Drawing Sheets

(51) Int. Cl.
    *C25D 5/48*     (2006.01)
    *C25D 7/00*     (2006.01)
    *G01N 27/30*     (2006.01)
    *G01N 33/53*     (2006.01)
    *G01N 33/543*     (2006.01)

(56) References Cited

OTHER PUBLICATIONS

L. Kashefi-Kheyrabadi, et al., "A microfluidic electrochemical aptasensor for enrichment and detection of bisphenol A", Biosensors and Bioelectronics, 117, p. 457-463, Oct. 2018.*

N. Mphuthi, et al., "Functionalization of 2D MoS2 Nanosheet with Various Metal and Metal Oxide Nanostructures: Their Properties and Application in Electrochemical Sensors", Biosensors, 12(6): p. 386-1-386-45, Jun. 2022.*

Shu, Yun, et al., "MoS2 Nanosheets-Au Nanorods Hybrids for Highly Sensitive Amperometric Detection of H2O2 in Living Cells", The Royal Society of Chemistry 20 xx; Journal of Materials Chemistry B; published Jan. 4, 2017; downloaded Aug. 1, 2017; pp. 1-9; DOI: 10.1039/C6TB02886A.

\* cited by examiner

ELECTROCHEMICAL APTASENSOR FOR DEHP DETECTION CONTAINING GOLD NANOFLOWERS

CROSS-REFERENCE TO RELATED APPLICATIONS

This application claims priority to and the benefit of Korean Patent Application No. 10-2021-0154747, filed on Nov. 11, 2021, in the Korean Intellectual Property Office, the disclosure of which is incorporated herein by reference in its entirety.

TECHNICAL FIELD

The following disclosure relates to an electrochemical aptasensor for detecting di(2-ethylhexyl)phthalate (DEHP) with high sensitivity.

BACKGROUND

The statements in this section merely provide background information related to the present disclosure and may not constitute prior art.

Production of plastics has continuously increased since the 1950s, and serious problems related to environmental pollution are occurring due to indiscreet use. About 300 million tons of plastic waste is produced worldwide every year, but only 9% of the plastic waste is recycled, and the rest is discharged into nature.

Phthalate or phthalic acid ester (PAE) is widely used as a plasticizer, and accounts for 70% of the global plasticizer market. PAE of these is used for manufacturing polyvinyl chloride (PVC), food packaging, cosmetics, electronic products, toys, and the like, and di(2-ethylhexyl)phthalate (DEHP) of PAE is a phthalate accounting for 37.1% of a plasticizer market share. DEHP acts as an endocrine disrupting chemical (EDC) to cause numerous problems including cancer and metabolic disorder.

Among various methods for detecting the DEHP, an electrochemical method is one of the preferred methods for detecting DEHP, due to the advantages such as high sensitivity, selectivity, simple operation, and low cost. In order to detect DEHP, various electrochemical sensors have been developed based on the characteristics. In order to detect a polar molecule having a specific size, a DEHP electrochemical sensor based on β-cyclodextrin (β-CD) has been developed, but sensing performance is deteriorated without a DEHP-specific receptor.

An aptamer is considered for high-sensitivity analysis of DEHP, but electrochemical impedance spectroscopy (EIS) is used for detecting low-concentration DEHP, and EIS further needs a potential difference mode, and needs a complicated process for data analysis.

Therefore, in order to develop a sensor for preventing health problems from exposure to a trace amount of DEHP and having high utility, DEHP eluted from a plastic product should be studied, and a study for a simple and sensitive electrochemical aptasensor for detecting DEHP migrating from a plastic product to water in everyday use is needed.

SUMMARY

An embodiment of the present invention is directed to providing an electrochemical aptasensor for high sensitivity detection of DEHP.

Another embodiment of the present invention is directed to providing a method of producing an electrochemical aptasensor for high sensitivity detection of DEHP by a simple method.

In one general aspect, an electrochemical aptasensor includes: a working electrode which is surface-modified with a graphene nanoplatelet composite including: graphene nanoplatelets, a transition metal chalcogen compound, and an amine-based polymer; gold nanoflowers bound to an upper end of the working electrode; and an aptamer which is capable of binding to a target material and is immobilized on the gold nanoflowers.

In the electrochemical aptasensor of the present invention, the transition metal may be selected from the group consisting of Mo, W, Ti, Tc, Hf, Zr, Re, Pd, and Pt, the chalcogen may be selected from the group consisting of S, Se, and Te, and the amine-based polymer may be selected from the group consisting of chitosan, chitin, polyaniline, polylysine, polyallylamine, polyethyleneimine, and poly(2-dimethylaminoethyl methacrylate).

In the electrochemical aptasensor of the present invention, the target material may be di(2-ethylhexyl)phthalate (DEHP), and a label molecule may be further bound to the aptamer.

In the electrochemical aptasensor of the present invention, a thiol-based molecule may be further bound to the gold nanoflowers, and the gold nanoflowers may have an average diameter of 0.1 to 10 µm.

In another general aspect, a method of producing an electrochemical aptasensor includes: (a) depositing a graphene nanoplatelet composite including: graphene nanoplatelets, a transition metal chalcogen compound, and an amine-based polymer on a working electrode; (b) electrodepositing a gold precursor on the working electrode to produce gold nanoflowers; and (c) immobilizing an aptamer capable of binding to a target material on the gold nanoflowers.

In the method of producing an electrochemical aptasensor of the present invention, after the immobilizing of the aptamer of (c), (d) further introducing a thiol-based molecular may be included.

In the method of producing an electrochemical aptasensor of the present invention, the gold precursor may be electrodeposited for 400 to 800 seconds to produce the gold nanoflowers in (b), the gold precursor may be electrodeposited with a voltage of −0.4 to 0.2 V to produce the gold nanoflowers in (b), and a concentration of the gold precursor for producing the gold nanoflowers may be 1 to 20 mM in (b).

In still another general aspect, a method of analyzing a target material includes: (a) preparing a sample for analysis; (b) injecting the prepared sample for analysis into the electrochemical aptasensor; (c) forming a composite by a target material specifically binding to an aptamer immobilized on a working electrode; and (d) measuring an electrochemical signal produced by the composite to analyze the target material in the sample for analysis.

In the method of analyzing a target material of the present invention, the target material may be di(2-ethylhexyl)phthalate (DEHP).

Other features and aspects will be apparent from the following detailed description, the drawings, and the claims.

BRIEF DESCRIPTION OF THE DRAWINGS

In order that the disclosure may be well understood, there will not be described various forms thereof, given by way of example, reference being made to the accompanying drawings, in which.

DETAILED DESCRIPTION

Figure 1:
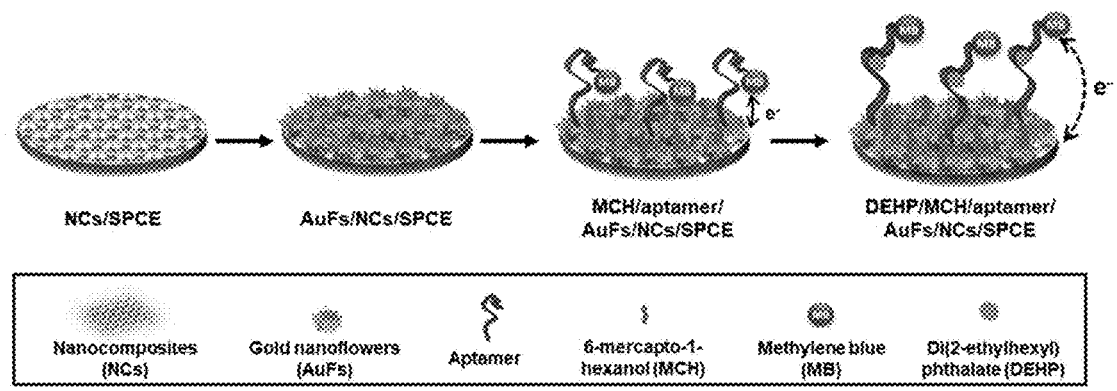
FIG. 1 is a schematic diagram of an electrochemical aptasensor of the present invention.

Hereinafter, the electrochemical aptasensor of the present invention will be described in detail with reference to the accompanying drawing.

The drawings to be provided herein are provided by way of example so that the spirit of the present invention can be sufficiently transferred to a person skilled in the art to which the present invention pertains. Therefore, the present invention is not limited to the drawings provided herein but may be embodied in many different forms, and the drawings suggested herein may be exaggerated in order to clear the spirit of the present invention.

Technical terms and scientific terms used herein have the general meaning understood by those skilled in the art to which the present invention pertains, unless otherwise defined, and the description for the known function and configuration which may unnecessarily obscure the gist of the present invention will be omitted in the following description and the accompanying drawings.

In addition, the singular form used in the specification and claims appended thereto may be intended to include a plural form also, unless otherwise indicated in the context.

In the present specification and the appended claims, the terms such as "first" and "second" are not used in a limited meaning but are used for the purpose of distinguishing one constituent element from other constituent elements.

In the present specification and the appended claims, the terms such "comprise" or "have" mean that there is a characteristic or a constituent element described in the specification, and as long as it is not particularly limited, a possibility of adding one or more other characteristics or constituent elements is not excluded in advance.

In the present specification and the appended claims, when a portion such as a membrane (layer), a region, and a constituent element is present on another portion, not only a case in which the portion is in contact with and directly on another portion but also a case in which other membranes (layers), other regions, other constitutional elements are interposed between the portions is included.

The electrochemical aptasensor of the present invention is characterized by including: a working electrode which is surface-modified with a graphene nanoplatelet composite including: graphene nanoplatelets, a transition metal chalcogen compound, and an amine-based polymer; gold nanoflowers bound to an upper end of the working electrode; and an aptamer which is capable of binding to a target material and is immobilized on the gold nanoflowers.

In a specific example, the working electrode may be used without limitation as long as it may be used in a sensor such as gold, palladium, silicon, and carbon electrodes, but it is most preferred to use a carbon electrode. Here, any method of forming a working electrode may be used without limitation as long as it is a method used in an electrochemical sensor, such as sputtering, screen printing, and inkjet printing.

In a specific example, the working electrode may be surface-modified with a graphene nanoplatelet composite. Here, the graphene nanoplatelet composite may include graphene nanoplatelets, a transition metal chalcogen compound, and an amine-based polymer. By the configuration, a self-aggregation of graphene by van der Waals force is decreased to increase adhesion to an electrode, thereby improving the mechanical properties and the electrical properties of a material.

In a specific example, the transition metal chalcogen compound (transition metal dichalcogenides, TMDC) which may be included in the graphene nanoplatelet composite refers to a compound having a chemical formula of $MX_2$ in which two chalcogen elements (X, Group 16 of the periodic table) are connected to one transition metal element (M) by a covalent bond. The electrochemical aptasensor of the present invention forms a composite in which a transition metal chalcogen compound having a band gap is bound to graphene nanoplatelets having no band gap, so that the electrical properties may be maintained excellent even with a band gap change by doping and the like.

In the transition metal chalcogen compound ($MX_2$) according to the present invention, the transition metal (M) may be selected from the group consisting of Mo, W, Ti, Tc, Hf, Zr, Re, Pd, and Pt, and chalcogen (X) may be selected from the group consisting of S, Se, and Te. Therefore, a non-limiting example of the transition metal chalcogen compound ($MX_2$) may include a compound selected from the group consisting of $MoS_2$, $MoSe_2$, $WS_2$, $WSe_2$, $TiS_2$, $TiSe_2$, $TiTe_2$, $HfS_2$, $HfSe_2$, $HfTe_2$, $ZrS_2$, $ZrSe_2$, $ZrTe_2$, $TcS_2$, $TcSe_2$, $TcTe_2$, $ReS_2$, $ReSe_2$, $ReTe_2$, $PdS_2$, $PdSe_2$, $PtS_2$, and $PtSe_2$, and preferably may be $MoS_2$. By selecting the transition metal chalcogen compound, a high electron transfer rate, flexibility, improved mechanical strength, relatively low toxicity, and a large surface area may be secured.

In a specific example, a non-limiting example of the amine-based polymer which may be included in the graphene nanoplatelet composite may include a compound selected from the group consisting of chitosan, chitin, polyaniline, polylysine, polyallylamine, polyethyleneimine, and poly(2-dimethylaminoethyl methacrylate), and preferably, may be chitosan. By selecting the amine-based polymer, it may have the low solubility in water, have biocompatibility, and act as an adhesive in binding the graphene nanoplatelets and the transition metal chalcogen compound.

When the graphene nanoplatelets, the transition metal chalcogen compound, and the amine-based polymer are included in the graphene nanoplatelet composite, the amine-based polymer may act as a binder in forming a composite of the graphene nanoplatelets and the transition metal chalcogen compound, and when gold nanoflowers are applied on the upper end of the working electrode which is surface-modified with the graphene nanoplatelet composite, a covalent bond to the gold nanoflowers is formed to apply the gold nanoflowers stably on the composite.

The graphene nanoplatelets and the transition metal chalcogen compound may be included at a content ratio of 1:0.1 to 5, preferably 1:0.5 to 3, and more preferably 1:1 to 2.5 by weight in the graphene nanoplatelet composite. When they are included in the range of content ratio, charge transfer resistance of a sensor surface may be lowered.

In addition, the content of each of the graphene nanoplatelets, the transition metal chalcogen compound, and the amine-based polymer may be 1:0.1 to 5:0.01 to 1, preferably 1:0.5 to 3:0.05 to 0.5, and more preferably 1:1 to 2.5:0.08 to 0.2. When the content range is satisfied, a high reduction current peak is shown, whereby the sensitivity of an electrode may be improved to show excellent accuracy in quantitative analysis of a target material with an electrochemical signal.

In a specific example, gold nanoflowers may be bound to the upper end of the working electrode. By binding the gold nanoflowers to the upper end of the working electrode, an aptamer for detecting a target material may be immobilized more stably, and a transfer rate of electrons produced as a result of an oxidation reduction reaction is increased to exert a synergy effect on sensitivity improvement of the target material. In addition, the gold nanoflowers are bound, thereby increasing an electrode active site to lower the detection limit of the working electrode to implement a high-sensitivity electrode sensor.

Here, the gold nanoflowers may have an average diameter of 0.1 to 2 µm, preferably 0.4 to 1.6 µm, and most preferably 0.6 to 0.8 µm.

In a specific example, the aptamer capable of binding to the target material may be immobilized in the electrochemical aptasensor of the present invention.

The aptamer of the electrochemical aptasensor according to the present invention refers to a nucleic acid which may specifically strongly bind to the target material while maintaining a stable three-dimensional structure and is also called, a chemical antibody, and may be easily structurally modified as compared with a single antibody and is easily synthesized and stable. The aptamer strongly immobilizes the target material by a G-rich group, and free binding and separation of the target material are easy by using the nature of the aptamer of releasing the structure by a high temperature or a high salt concentration. A functional group selected from the group consisting of an amine group, a carboxyl group, a hydroxyl group, and a thiol group may be attached to the aptamer so that the aptamer may be immobilized on the gold nanoflowers applied on the working electrode of the electrochemical aptasensor.

Figure 2:
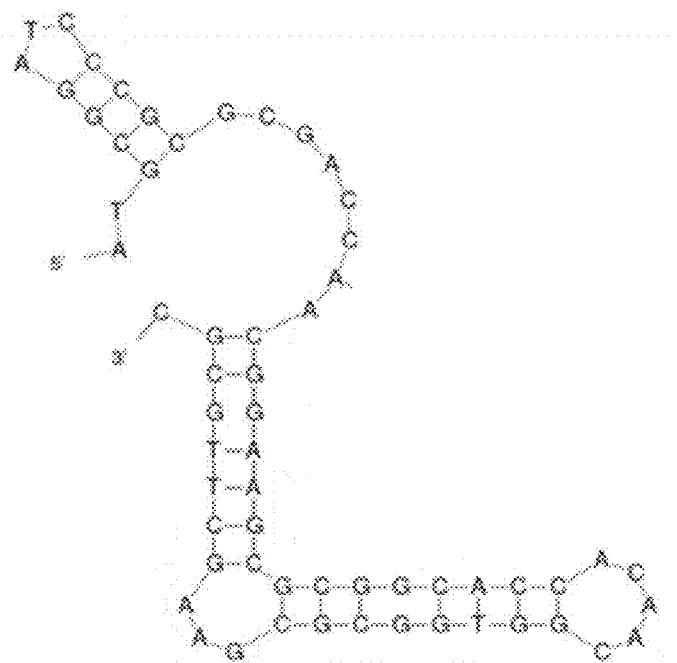
FIG. 2 is a drawing showing an aptamer used in the electrochemical aptasensor of the present invention.

In a specific example, any target material may be used without limitation as long as it may be a target of the aptamer, and preferably, may be di(2-ethylhexyl)phthalate (DEHP). Therefore, the aptamer of the electrochemical aptasensor according to the present invention may be used without limitation as long as the aptamer has a specific affinity to DEHP, but preferably, may be a PT01 aptamer. The specific structure of the PT01 aptamer is shown in FIG. 2.

In a specific example, a label molecule may be further bound to the aptamer for detecting DEHP. More specifically, DEHP is bound to the aptamer, and the shape of the aptamer changes as DEHP is bound. Here, as the shape of the aptamer changes, the position of a secondary signal transduction material changes as a label molecule bound to DEHP. The label molecule as such is one of the materials which may transfer current and is injected as a secondary signal transduction material after the target material is bound, when current occurs, it may be confirmed the target material is successfully bound. Besides, it is also possible to quantitatively evaluate the target material by the change of electrochemical signal quantity. A non-limiting example of the secondary signal transduction material which may be used as a label molecule may be methylene blue (MB).

In a specific example, a thiol-based molecule may be further bound to the gold nanoflowers. The thiol-based molecule may be a molecule including a thiol group in a branch, and it is most preferred to select 6-mercapto-1-hexanol (MCH). When the thiol-based molecule is further bound to the gold nanoflowers, the surface of the sensor is passivated to prevent non-specific binding, and thus, DEHP and the aptamer may specifically react.

The method of producing an electrochemical aptasensor of the present invention is characterized by including: (a) depositing a graphene nanoplatelet composite including: graphene nanoplatelets, a transition metal chalcogen compound, and an amine-based polymer on a working electrode; (b) electrodepositing a gold precursor on the working electrode to produce a gold nanoflowers; and (c) immobilizing an aptamer capable of binding to a target material on the gold nanoflowers.

In a specific example, the working electrode which is surface-modified with graphene nanoplatelets in (a) may be produced by preparing an amine-based polymer solution, mixing graphene and a transition metal chalcogen compound with the solution to prepare a uniform dispersion, and then spin coating or drop coating the dispersion.

In a specific example, the step of electrodepositing a gold precursor to produce gold nanoflowers in (b) may be performed by any one or more methods selected from the group consisting of chemical vapor deposition (CVD), atomic layer deposition, sputtering, laser ablation, electrochemical welding, arc-discharge, plasma deposition, thermochemical vapor deposition, and electron beam vapor deposition, but is not particularly limited thereto. Preferably, it may be application by electrochemical welding by constant potential processing for a certain time in a sulfuric acid solution and a gold precursor ($HAuCl_4 \cdot 3H_2O$) solution.

Here, the concentration of the gold precursor solution for producing the gold nanoflowers may be 1 to 20 mM, preferably 3 to 18 mM, and most preferably 5 to 15 mM.

In addition, the gold precursor may be electrodeposited for 400 to 800 seconds, preferably 450 to 750 seconds, and most preferably 500 to 700 seconds, for producing the gold nanoflowers.

In addition, the gold precursor may be electrodeposited at a voltage of −0.2 to 0.4 V, preferably 0 to 0.35 V, and most preferably 0.1 to 0.3 V for producing the gold nanoflowers.

When the concentration, the electrodeposition time, and the electrodeposition voltage of the precursor solution in the above ranges are satisfied, it may advantageously act on the immobilization of the aptamer without inhibition of an interaction between the graphene nanoplatelet composite and the gold nanoflowers.

In a specific example, (d) introducing a thiol-based molecule may be further included, after immobilizing an aptamer in (c).

The present invention provides a method of analyzing a target material by using the aptasensor. Hereinafter, a method of analyzing a target material depends on the aptasensor according to the present invention described above and includes the characteristics of the configurations described above, and overlapping description will be omitted.

Specifically, the method of analyzing a target material of the present invention includes: (a) providing a sample for analysis; (b) injecting the sample for analysis into a sensor for detecting the target material; (c) forming a composite by the target material specifically binding to an aptamer immobilized on a working electrode; and (d) measuring an electrochemical signal produced by the composite to analyze the target material in the sample for analysis, wherein the working electrode includes graphene nanoplatelets, a transition metal chalcogen compound, and an amine-based polymer.

Hereinafter, the present invention will be described in detail by the examples. However, the examples are for describing the present invention in more detail, and the scope of the present invention is not limited to the following examples.

<Production Example> Production of AuS/NC/SPCE Working Electrode

Before the surface of the electrode was modified, a screen printed carbon electrode (SPCE) was electrochemically washed until a stable voltammetric method was obtained by cyclic voltammetry (CV) over a range of −0.1 to 0.7 V in a 0.5 M $H_2SO_4$ solution. After drying with nitrogen gas, 20 μL of a nanocomposite (NC) including a $MoS_2$ nanosheet, graphene nanoplatelets (GNP), and chitosan (CHT) at a content ratio of 2:1:0.1 by weight was prepared, and then was added dropwise to a working electrode. After complete drying, the working electrode was washed with deionized water and dried using nitrogen gas to remove the residue. Thereafter, $HAuCl_4 \cdot 3H_2O$ in 0.5 M $H_2SO_4$ was electrodeposited on NC/SPCE to form a gold nanostructure (AuS). Then, a gold nanostructure (AuS) was formed under various electrodeposition conditions using variables of 5 to 20 mM of a gold precursor, a deposition time of 120 to 600 seconds, and applied potential of −0.4 to 0.4 V.

<Example> Production of Aptasensor Including AuS/NC/SPCE Working Electrode

An aptamer solution was heated at 95° C. for 5 minutes and cooled at 23° C. for 15 minutes. After the aptamer was immobilized, 1.4 μL of a 5 mM tris(2-carboxyethyl)phosphine hydrochloride (TCEP) solution was mixed with 5.6 μL of 5 μM aptamer solution. The solution was incubated for 1 hour for cutting a 5'-disulfide bond. Subsequently, 7 μL of a TCEP-aptamer mixed solution was drop cast on AuS/NC/SPCE, and incubated at 23° C. for 2 hours. Then, a working electrode was treated with 6-mercapto-1-hexanol (MCH, 0.1 mM in 1×phosphate buffered saline (PBS) at pH 7.4) for 10 minutes for preventing non-specific binding. Finally, 7 μL of a target molecule (DEHP) of various concentrations in deionized water was introduced to the surface of MCH/aptamer/AuS/NC/SPCE at 23° C. for 40 minutes.

<Experimental Method>

1. Electrochemical Experiment

All electrochemical experiments used a 3-electrode system at 23° C. An aptasensor was observed by performing CV at a scan speed of 0.1 V/s over a range of −0.3 to 0.4 V in a $K_3[Fe(CN)_6]$ ($5\times10^{-3}$ M) solution including 0.1 M potassium chloride (KCl). DPV was performed using a pulse amplitude of 0.05 V, a pulse width of 0.05 seconds, and a pulse period of 0.5 seconds. An electrochemical reaction of methylene blue (MB) joined to the aptamer was observed using a pulse amplitude of 0.05 V, a pulse width of 0.05 seconds, and a pulse period of 0.5 seconds over a range of −0.8 to −0.1 V at a scan speed of 0.1 V/s using a 0.10 M PBS solution including 0.10 M KCl.

2. DEHP Migration and LLE-GC-MS Analysis

A phenomenon in which DEHP migrates to water was studied using various plastic samples. A sample was cut into pieces of ~1×1 cm (~1 g), which were added to deionized water in a colored glass bottle with a Teflon coating cap for preventing contamination from other phthalates. The bottle was shaken twice a day for uniform distribution of DEHP which had migrated. After incubation at 23° C. for 24 hours, water to which DEHP had migrated was filtered using nitrocellulose filter paper of 24 μm to remove plastic pieces of debris, thereby preventing further discharge of DEHP into water. The reliability of the electrochemical method was determined by comparing the results of the electrochemical experiment and the conventional LLE-GC-MS.

The GC-MS analysis of DEHP which had migrated was performed using ethyl acetate. To this end, 20 mL of water to which DEHP had migrated was diluted with ethyl acetate, shaken for 10 minutes, and centrifuged at 2500 rpm for 5 minutes. The produced solution showed an organic phase and an aqueous phase, and an organic (ethyl acetate) layer was separated therefrom and remaining moisture was removed using sodium sulfate. The volatile solution was used for measuring the DEHP concentration of the sample which had migrated thereafter.

Figure 3:
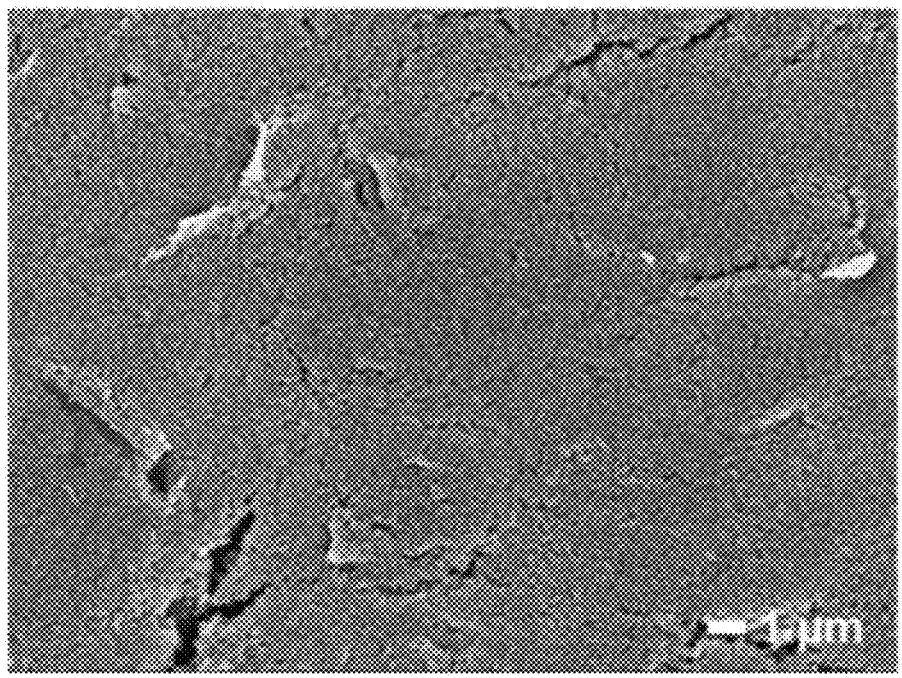
FIG. 3 is FE-SEM image of SPCE.

<Experimental Example 1> Analysis of Characteristics of AuS/NC/SPCE Working Electrode First, the surface of NC/SPCE on which SPCE, NC/SPCE, and AuS were electrodeposited was observed by FE-SEM, and the results are shown in FIG. 3.

Figure 4:
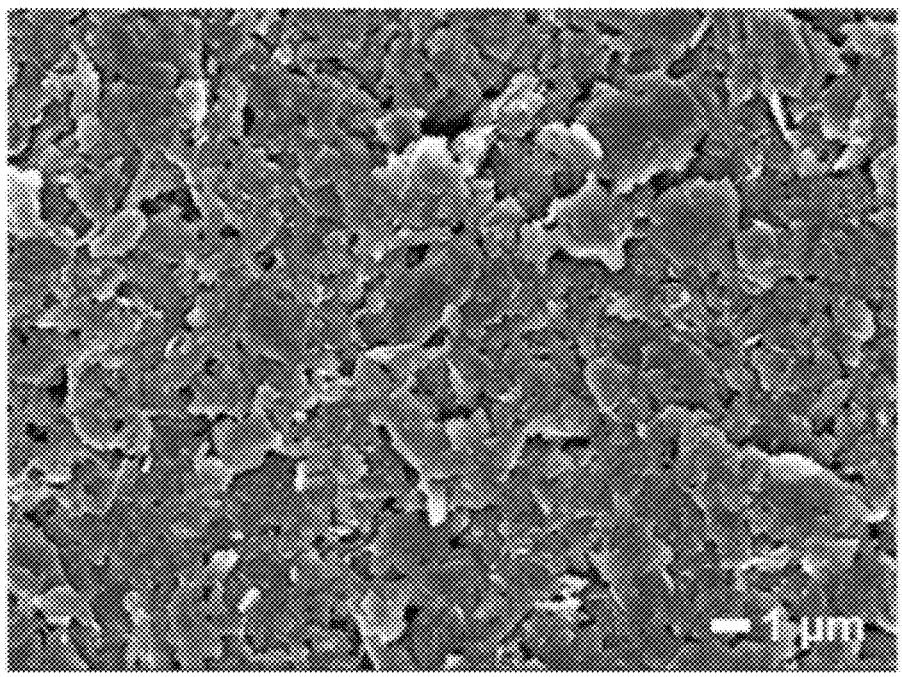
FIG. 4 is FE-SEM image of NC/SPCE.

Referring to the FE-SEM image of SPCE in FIG. 3, a porous surface with defects is observed, which shows a typical characteristic of a carbon electrode surface. However, referring to the FE-SEM image of NC/SPCE in FIG. 4, the surface of the electrode became rough and a structure laminated with a flaked single layer is seen by including a $MoS_2$ nanosheet and GNP in NC. That is, it was confirmed that the surface of SPCE to which NC was introduced had a large surface area.

Next, AuS was electrodeposited on the surface of NC/SPCE, and the electrodeposited surface was analyzed by three variables of the concentration of the gold precursor, an electrodeposition time, and an applied voltage. In order to obtain a high conductivity of the surface and a high surface to volume ratio, optimal electrodeposition conditions were selected, and a gold precursor concentration of 10 mM at 600 seconds was applied to observe an effect of voltage applied between −0.4 V and 0.4 V for an Ag reference electrode. AuS electrodeposition followed the following reaction:

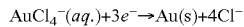

Figure 5:
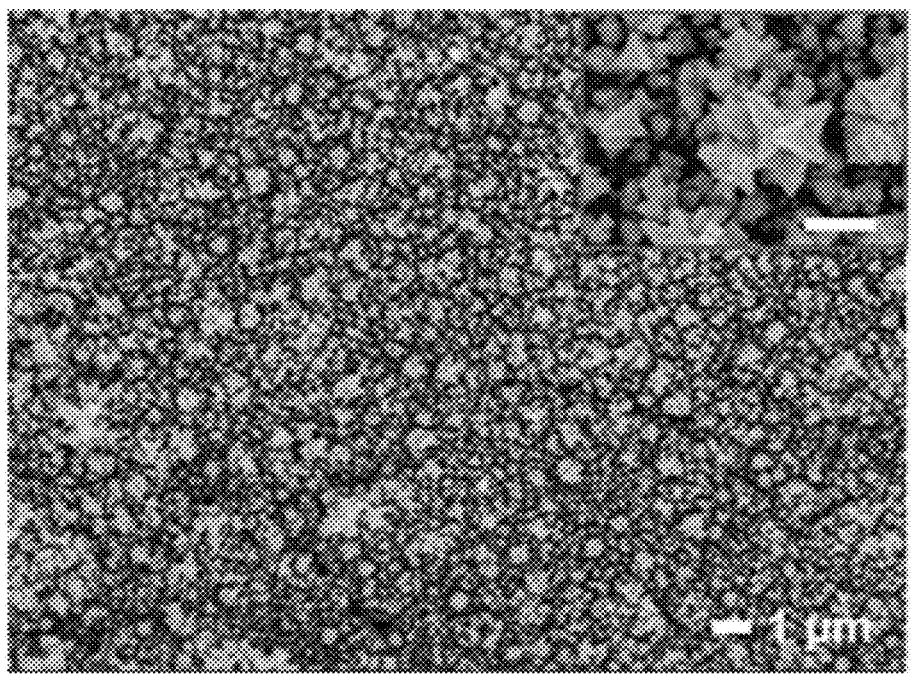
FIG. 5 is FE-SEM image of AuS/NC/SPCE obtained by electrodepositing a 10 mM gold precursor solution at a voltage of −0.2 V for 600 seconds.

Referring to the FE-SEM image of AuS/NC/SPCE on which AuS was electrodeposited at −0.2 V in FIG. 5, it was confirmed that small-sized AuS was electrodeposited unevenly at high overpotential (−0.2 V). This is because when high overpotential is applied, abundant nucleation is induced all over the surface for a short time with high energy, and rapid consumption of $Au^{3+}$ is caused before AuS is uniformly grown, thereby forming small and irregular AuS.

Figure 6:
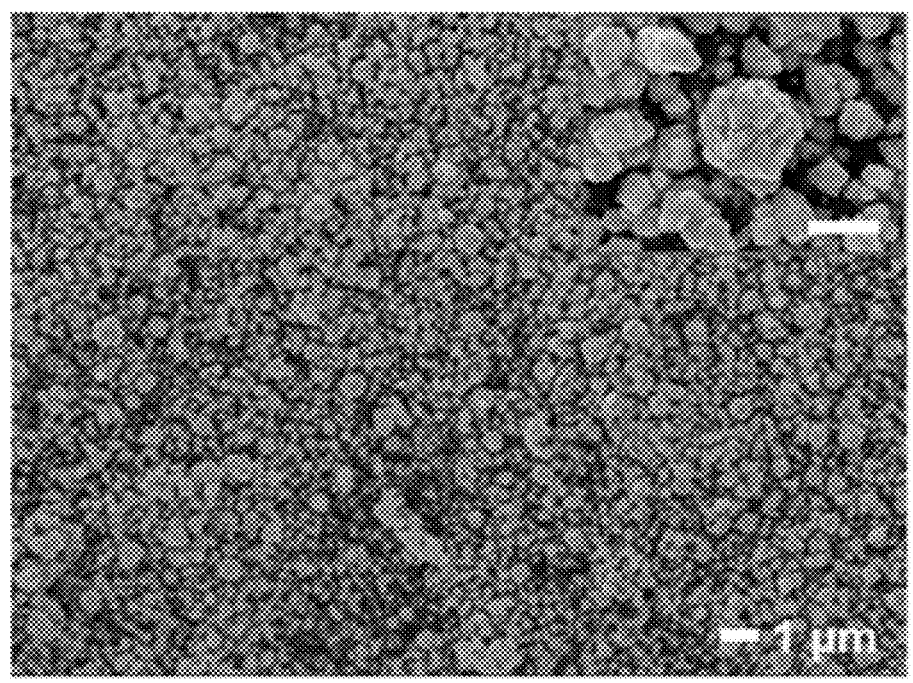
FIG. 6 is FE-SEM image of AuS/NC/SPCE obtained by electrodepositing a 10 mM gold precursor solution at a voltage of 0 V for 600 seconds.
Figure 7:
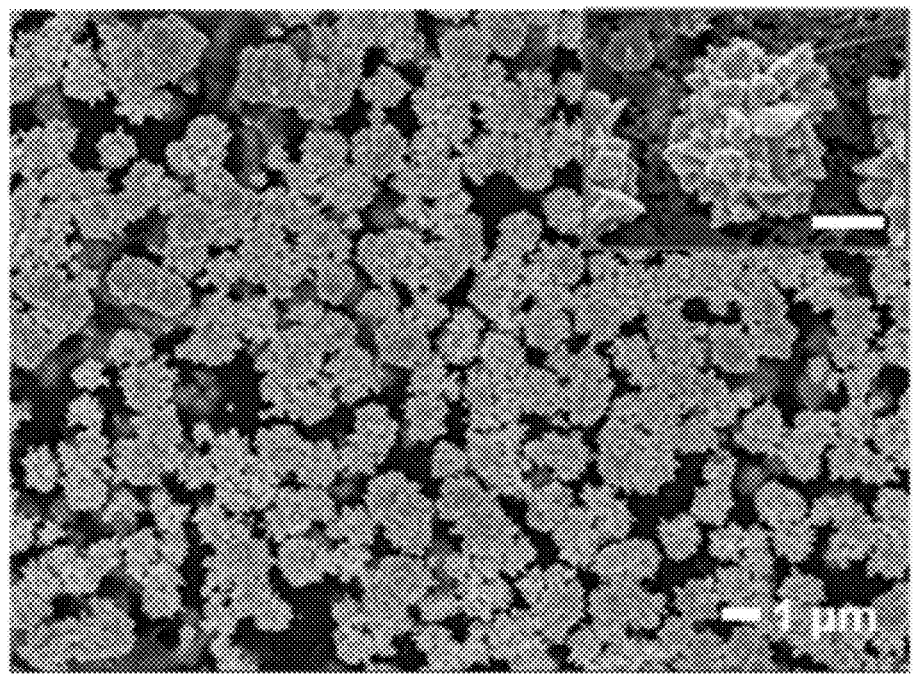
FIG. 7 is FE-SEM image of AuS/NC/SPCE obtained by electrodepositing a 10 mM gold precursor solution at a voltage of 0.2 V for 600 seconds.

In contrast, referring to the FE-SEM image of AuS/NC/SPCE on which AuS was electrodeposited at 0 V and 0.2 V in FIG. 6 and FIG. 7, it was confirmed that clustered AuS and flow-shaped AuS were formed at low overpotential (0 V) and lower overpotential (0.2 V), respectively. At low overpotential, a small number of nuclei are formed during initial electrodeposition due to insufficient energy, and $Au^{3+}$ is reduced on the existing nuclear surface and grows first rather than nucleation during residual electrodeposition.

As a result, large AuS homogeneously grew at low overpotential. Three shapes were observed based on the FE-SEM images of AuS formed at different potentials, and are expressed as nano-leaf (AuL), nano-cluster (AuC), and nano-flower (AuF), respectively as in FIG. 5 to FIG. 7.

Next, the chemical compositions of AuL, AuC, and AuF which were formed at different electrodeposition voltages were analyzed by EDS, and the results are shown in Table 1:

TABLE 1

| Potential (V vs. Ag) | −0.2 | 0 | 0.2 |
|---|---|---|---|
| Shape of gold nanostructure | Nano-leaf (AuL) | Nano-cluster (AuC) | Nano-flower (AuF) |
| Content of gold (mass %) | 61.42 | 67.61 | 70.75 |

Referring to Table 1, it was confirmed that the weight ratios of Au were measured as 61.42%, 67.61%, and 70.75%, respectively, with the potential change, and it was found therefrom that the content of gold was the highest at the electropotential of 0.2 V.

Figure 8:
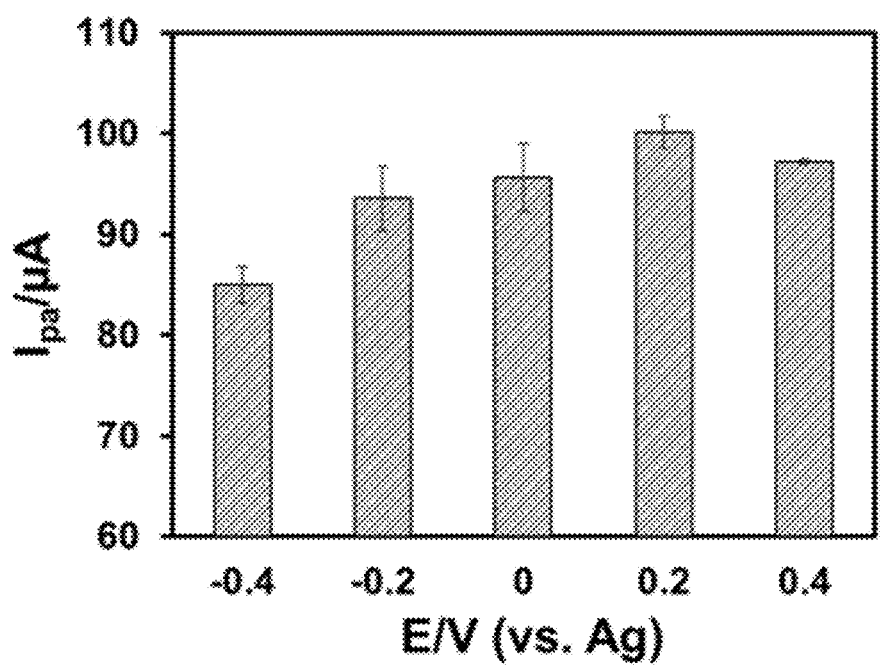
FIG. 8 is a graph showing anode peak currents at different electrodeposition voltages.

In addition, the results of performing CV analysis for comparing the anodic peak current ($i_{pa}$) of $K_3[Fe(CN)_6]$ ($5 \times 10^{-3}$ M) including 0.10 M KCl, using the AuS/NC/SPCE electrode are shown in FIG. 8. Referring to FIG. 8, the highest anode peak current (100.20±1.59 μA) was measured in the AuS/NC/SPCE electrode to which a voltage of 0.2 V had been applied, and it was confirmed therefrom that the flower-shaped nanoflowers formed in the AuS/NC/SPCE electrode to which a voltage of 0.2 V had been applied provided a large surface area to show excellent electrical conductivity. Thus, it was used as an optimal variable to apply a deposition voltage of 0.2 V with a gold precursor concentration of 10 mM and a deposition time of 600 seconds.

Figure 9:
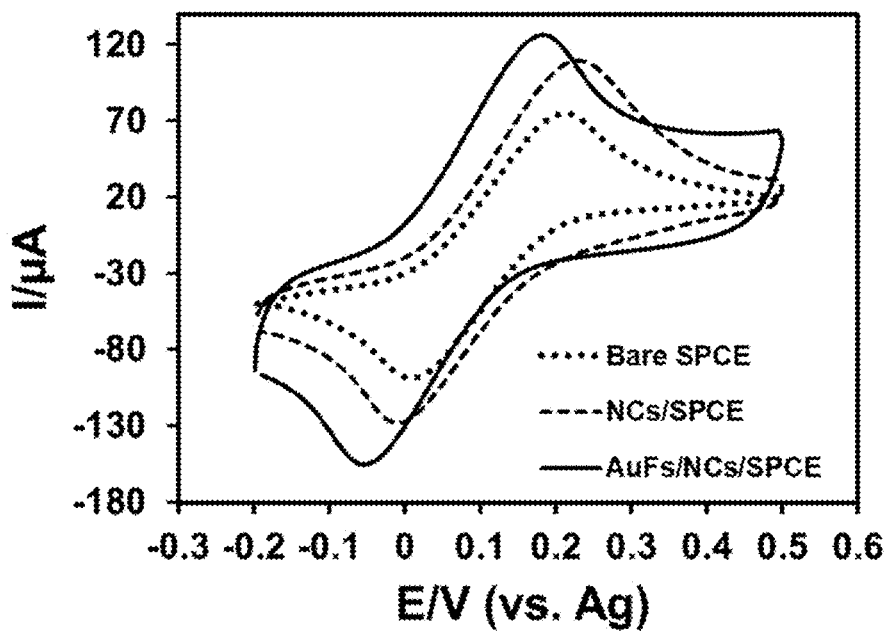
FIG. 9 is a CV graph of SPCE, NC/SPCE, and AuS/NC/SPCE.

Next, the results of studying the electrochemical performance of the AuF/NC/SPEC working electrode are shown in FIG. 9. Referring to FIG. 9, presence of a pronounced redox peak was confirmed in the CV curve of $K_3[Fe(CN)_6]$ ($5 \times 10^{-3}$ M) including 0.1 M KCl. In comparison with a pure SPCE electrode, NC/SPCE showed a high peak current, and the AuF/NC/SPCE working electrode on which AuF had been electrodeposited showed the highest peak current. It was confirmed from the results that the surface area to show the electrical activity in the AuF/NC/SPCE working electrode was increased, resulting in the increased in conductivity.

<Experimental Example 2> Analysis of Characteristics of Aptamer/AuS/NC/SPCE Sensor The electrochemical properties of AuF/NC/SPCE, aptamer/AuF/NC/SPCE, MCH/aptamer/AuF/NC/SPCE, and DEHP/MCH/aptamer/AuF/NC/SPCE were observed by CV.

Figure 10:
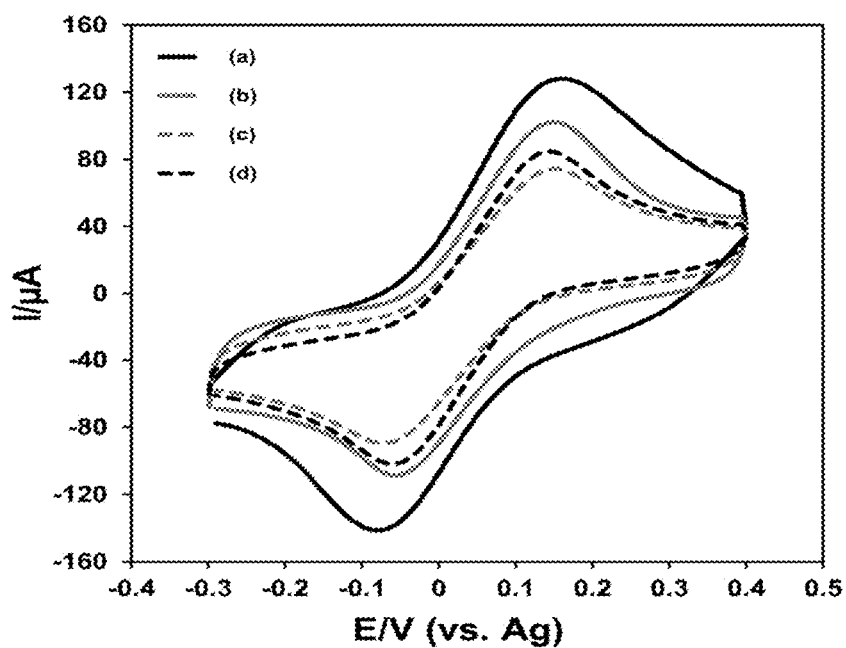
FIG. 10 is a CV graph of (a) AuF/NC/SPCE, (b) aptamer/AuF/NC/SPCE, (c) MCH/aptamer/AuF/NC/SPCE, and (d) DEHP/MCH/aptamer/AuF/NC/SPCEDML.

Referring to FIG. 10, curve (a) is a graph using AuF/NC/SPCE, shows a pair of redox peaks, and shows the highest peak current. This is because of high conductivity due to the redox of $K_3[Fe(CN)_6]$ and the enlarged surface area of the electrode modified with AuF.

Curve (b) is a graph using aptamer/AuF/NC/SPCE, and it was confirmed therefrom that peak current was decreased and the aptamer was immobilized on AuF. The decreased current occurred by the negatively charged phosphate skeleton of the aptamer.

Curve (c) is a graph using MCH/aptamer/AuF/NC/SPCE, and it was confirmed therefrom that when aptamer/AuFs/NCs/SPCE was treated with MCH for preventing non-specific binding, current was decreased. This is because the voids of the sensor surface were filled with MCH to block electron transfer.

Curve (d) is a graph using DEHP/MCH/aptamer/AuF/NC/SPCE, and it was confirmed therefrom that current increased again after DEHP was introduced. This means that electron transfer was facilitated by the specific binding of DEHP and the aptamer in the presence of DEHP.

<Experimental Example 3> Analysis of Aptasensor Performance

The performance of the MCH/aptamer/AuF/NC/SPCE sensor was evaluated by performing DPV in 0.1 M PBS including 0.1 M KCl after incubation with DEHP.

Figure 11:
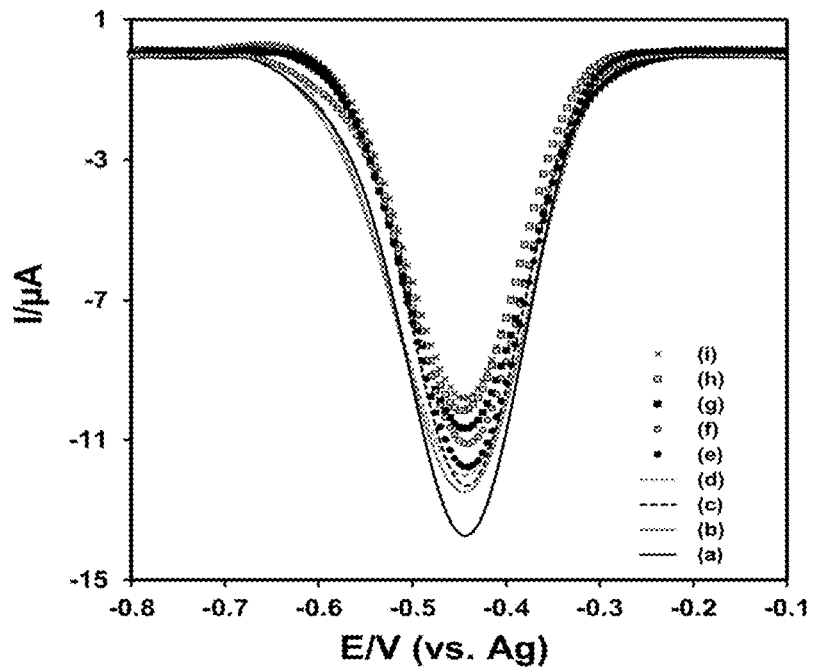
FIG. 11 is a DPV graph of MCH/aptamer/AuF/NC/SPCE at DEHP concentrations of (a) 0, (b) $0.5 \times 10^0$, (c) $1 \times 10^0$, (d) $1 \times 10^1$, (e) $1 \times 10^2$, (f) $1 \times 10^3$, (g) $1 \times 10^4$, (h) $1 \times 10^5$, and (i) $1 \times 10^6$ pg/mL.

Referring to FIG. 11, a DPV graph of MCH/aptamer/AuFs/NCs/SPCE treated with different concentrations of DEHP is shown. Since the DPV peak current tended to gradually decrease as the DEHP concentration increased from $0.5 \times 10^0$ to $1 \times 10^6$ pg/mL, the dependence of the electrochemical reaction on the DEHP concentration was shown. That is, it was confirmed that as the concentration of DEHP increased, the structural change in which methylene blue migrated away from the sensor surface occurred, resulting in a decrease in reduction current.

The results obtained shows the excellent performance of the aptasensor in a large range. The results confirmed that the aptasensor may be used without pretreatment or an additional step as compared with a method requiring cumbersome and bulky equipment such as chromatography.

Next, a signal corresponding to DEHP of $1 \times 10^3$ pg/mL was compared with signals corresponding to six interfering agents (benzylbutyl phthalate, BBP), diethyl phthalate (DEP), dimethyl phthalate (DMP), diphenyl phthalate (DPP), diisononyl phthalate (DINP), diisobutyl phthalate (DIBP) ($1\times10^4$ pg/m) to study the material specificity of the sensor.

Figure 12:
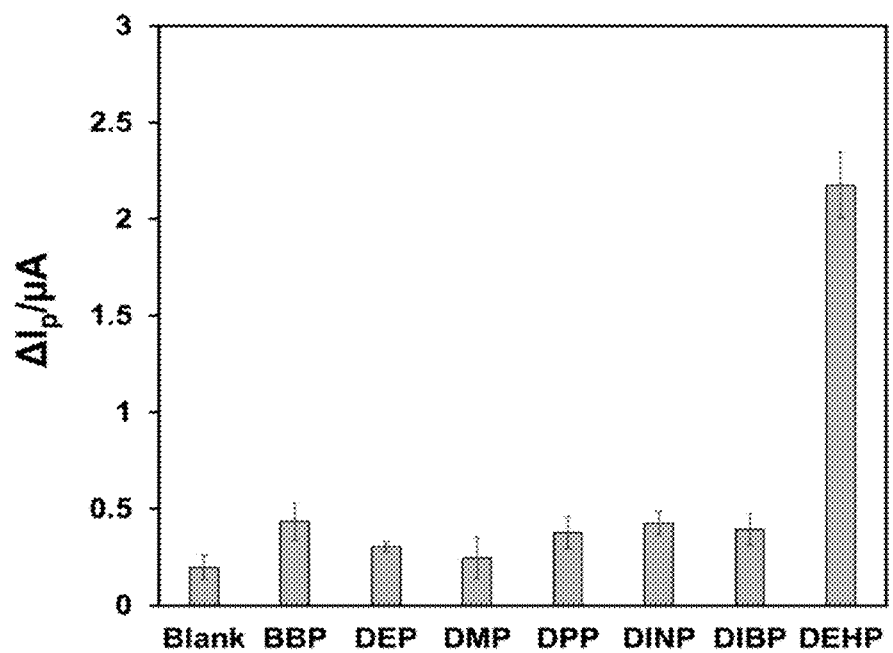
FIG. 12 is a graph showing DEHP specificity of the electrochemical aptasensor of the present invention.

Referring to FIG. 12, it was confirmed that a large signal change was shown in DEHP as compared with other species. Therefore, it was found that the aptasensor of the present invention showed high specificity to DEHP.

Figure 13:
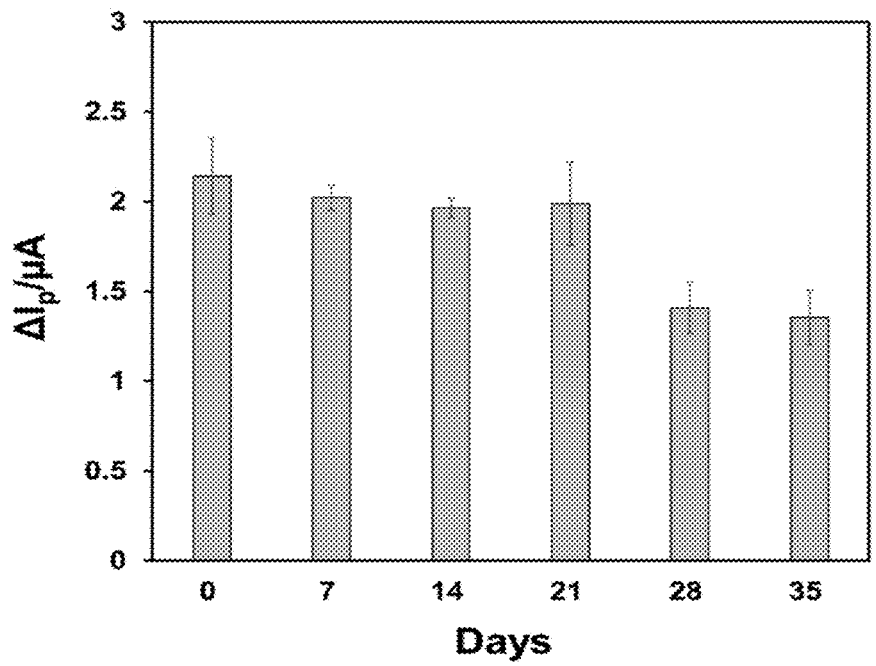
FIG. 13 is a graph showing stability of the electrochemical aptasensor of the present invention.

Next, the MCH/aptamer/AuFs/NCs/SPCE electrode was stored at 4° C. for 35 days, and $1\times10^3$ pg/mL of DEHP was incubated every 7 days in the electrode to perform stability evaluation. Referring to FIG. 13, it was confirmed that 93% of the original signal was maintained even after 21 days, and it was found that the stability was maintained during long-term storage.

<Experimental Example 4> Practical Application of Aptasensor

Figure 14:
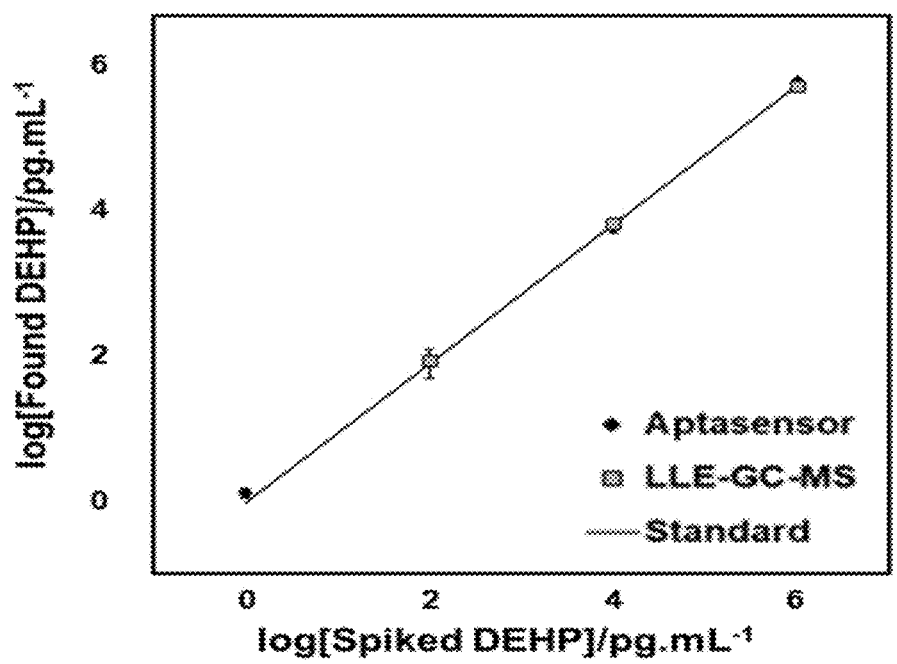
FIG. 14 is a graph in which DEHP is measured using the electrochemical aptasensor of the present invention and LLE-GC-MS.

The aptasensor was used for observing DEHP migrating from the plastic product used in practice. Before the observation, the accuracy of the aptasensor was verified by comparison with LLE-GC-MS. The concentration of spiked DEHP in deionized water was evaluated by DPV, and the obtained DPV current was changed to a DEHP concentration. It was confirmed that the results obtained by using the aptasensor and LLE-GC-MS showed a linear relationship as in FIG. 14, and thus, the aptasensor showed high accuracy at a level of LLE-GC-MS.

Next, 10 plastic products used in practice were selected, the amount of DEHP migrating from the plastic product to water was measured, and the results obtained using the aptasensor and LLE-GC-MS were compared.

Figure 15:
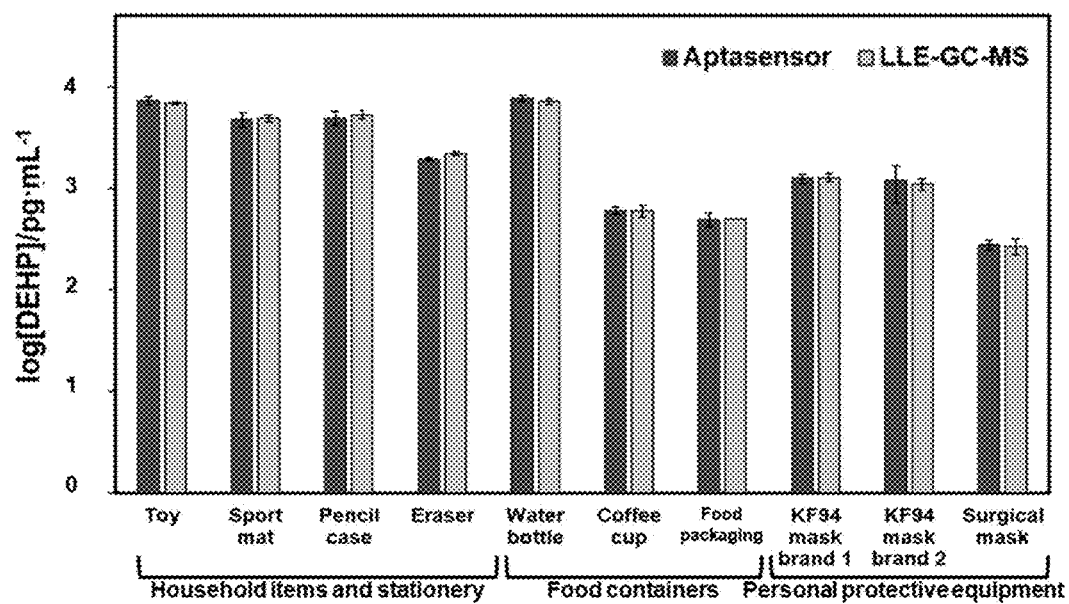
FIG. 15 is a graph in which DEHP migrating from a plastic product was measured using the electrochemical aptasensor of the present invention and LLE-GC-MS.

Referring to FIG. 15, the analysis results based on the aptasensor to DEHP migrating in a range of $2.76\times10^2$ to $7.75\times10^3$ pg/mL were confirmed, which shows a similar relationship to the results measured by LLE-GC-MS. A relative error of migrating DEHP between two methods was confirmed to be less than 11.68%, showing that the aptasensor of the present invention as well as LLE-GC-MS may be used as an observation tool for measuring a trace amount of DEHP.

The electrochemical aptasensor according to the present invention has a low detection limit concentration by improving sensitivity by sensor surface modification using a nano composite and gold nanoflowers, and has high practical applicability of a sensor by monitoring a trace amount of DEHP migrating from a real plastic product by a simple measurement method.

What is claimed is:

1. An electrochemical aptasensor comprising:
a working electrode which is surface-modified with a graphene nanoplatelet composite including: graphene nanoplatelets, a transition metal chalcogen compound, and an amine-based polymer;
gold nanoflowers bound to an upper end of the working electrode; and
an aptamer which is capable of binding to a target material and is immobilized on the gold nanoflowers.

2. The electrochemical aptasensor of claim 1, wherein the transition metal is selected from the group consisting of Mo, W, Ti, Tc, Hf, Zr, Re, Pd, and Pt.

3. The electrochemical aptasensor of claim 1, wherein the chalcogen is selected from the group consisting of S, Se, and Te.

4. The electrochemical aptasensor of claim 1, wherein the amine-based polymer is selected from the group consisting of chitosan, chitin, polyaniline, polylysine, polyallylamine, polyethyleneimine, and poly(2-dimethylaminoethyl methacrylate).

5. The electrochemical aptasensor of claim 1, wherein the target material is di(2-ethylhexyl)phthalate (DEHP).

6. The electrochemical aptasensor of claim 1, wherein a label molecule is further bound to the aptamer.

7. The electrochemical aptasensor of claim 1, wherein a thiol-based molecule is further bound to the gold nanoflowers.

8. The electrochemical aptasensor of claim 1, wherein the gold nanoflowers have an average diameter of 0.1 to 10 μm.

* * * * *